United States Patent [19]
Belli et al.

[11] Patent Number: 5,610,316
[45] Date of Patent: Mar. 11, 1997

[54] PROCESS FOR THE PREPARATION OF (−)-ESERETHOLE FROM MIXTURES OF (−) AND (+)-ESERETHOLE

[75] Inventors: Aldo Belli; Giorgio Chiodini; Stefano Maiorana, all of Milan, Italy

[73] Assignee: Laboratorio Chimico Internazionale S.p.A., Milan, Italy

[21] Appl. No.: 379,536

[22] PCT Filed: Jul. 20, 1993

[86] PCT No.: PCT/EP93/01908

§ 371 Date: Feb. 21, 1995

§ 102(e) Date: Feb. 21, 1995

[87] PCT Pub. No.: WO94/03457

PCT Pub. Date: Feb. 17, 1994

[30] Foreign Application Priority Data

Jul. 30, 1992 [IT] Italy ................. MI92A1861

[51] Int. Cl.$^6$ ................. C07D 209/00
[52] U.S. Cl. ................. 548/429
[58] Field of Search ................. 548/429

[56] References Cited

FOREIGN PATENT DOCUMENTS 899023  6/1962  United Kingdom .

OTHER PUBLICATIONS

Kobayashi, T. *Annalen der Chemie* pp. 143–163, (1938).

Dale, F. J. et al., J. Pharm. Pharmac., 1970, 22, pp. 889–896.

*Primary Examiner*—Jacqueline Haley
*Attorney, Agent, or Firm*—Bucknam and Archer

[57] ABSTRACT

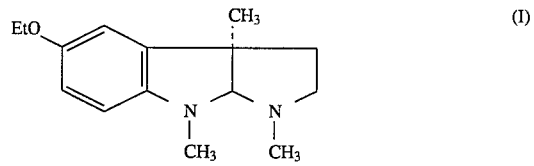

A process for the preparation of (−)-eserethole, of formula (I) starting from (+)-eserethole, or from mixtures of (±)-and (−)-eserethole in which the latter enantiomer prevails, by treating (±)-eserethole or mixtures of (+)-and (−)-eserethole enriched in the latter enantiomer, with 0.5–0.7 mole (per mole of the enantiomeric mixture) of a resolution agent, to yield a (−)-eserethole salt less soluble than the corresponding (+)-eserethole salt.

5 Claims, No Drawings

PROCESS FOR THE PREPARATION OF (−)-ESERETHOLE FROM MIXTURES OF (−) AND (+)-ESERETHOLE

This application is a National Stage application of PCT/EP93/01908 filed Jul. 20, 1993 and published as WO 94/03457 on Feb. 17, 1994.

The present invention relates to a process for the preparation of (−)-eserethole, of formula (I)

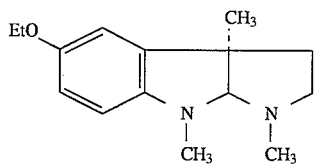

starting from (±)-eserethole, or from mixtures of (+)- and (−)-eserethole in which the latter enantiomer prevails.

(−)-Eserethole is known to be the main intermediate for the synthesis of (−)-eserine (physostigmine), which is a naturally occurring alkaloid of great interest for the treatment of Alzheimer'disease (see, for example, L. J. Thal and coll., N. Engl. J. Med. 308, 720 (1983) and Ann. Neurol. 13, 491 (1983); L. Gustarson and coll., Psychopharmacol. 93, 31 (1987)).

In literature (T. Kobayashi, Annalen der Chemie 143–163 (1938), the resolution of (±)-eserethole by means of tartaric acid, following a very laborious procedure and in unsatisfactory yields, is described. According to Kobayashi, (±)-eserethole is in fact treated in alcohol medium with (+)-tartaric acid in a 1:1 molar ratio. Therefor a mixture of (+)-eserethole (+)-tartrate and (−)-eserethole (+)-tartrate precipitates, the first one prevailing. This mixture must be recrystallized at least 5 times from alcohol, to obtain pure (+)-eserethole (+)-tartrate in a 50% yield. The mother liquors are alkalinized, the free base, which is enriched in (−)-eserethole, is distilled, then treated in alcohol with (−)-tartaric acid, in a 1:1 molar ratio. Thereby (−)-eserethole (−)-tartrate precipitates which is brought to a complete optical purity after one/two crystallizations, in a 18% yield. In practice, since the desired (−)-eserethole is obtained from said tartrate in a 98–99% yield, the process according to Kobayashi allows to obtain, from 100 g of racemate, only 9 g of (−)-eserethole (apart from any recovered material, involving of course even more complex procedures).

Now it has been found that optically pure (−)-eserethole can be obtained with markedly higher yields and easier procedures from mixtures of (−)- and (+)-eserethole (usually from (±)-eserethole), operating with a resolution agent amount lower than the stoichiometric amount, which amount ranges from 0.5 to 0.7 mole of the resolution agent by mole of (±)-eserethole, preferably about 0.6 mole of resolution agent by mole of (±)-eserethole.

Moreover, it has been found that the process is particularly simple compared with the known one, when operating with such resolution agents as to yield a (−)-eserethole salt less soluble than the (+)-eserethole one. Preferably, according to the invention, the resolution of (±)-eserethole, or of other enantiomeric mixtures, is carried out with a resolution agent selected from the group consisting of D-(−)-tartaric, D-(+)-malic and N-benzoyl-L-glutamic acids.

Particularly favourable results are obtained with the latter acid.

Suitable solvents according to the invention are lower alcohols (such as ethanol or isopropanol), lower ketones (such as acetone or methyl ethyl ketone), lower ethers (such as diethyl ether o diisopropyl ether), lower esters (such as ethyl acetate), or mixtures of said solvents.

The following example s further illustrate the process of the invention.

EXAMPLE 1

Use of D(−)tartaric acid (±)-Eserethole (2.46 g; 0.01 mole) is dissolved in 95% ethanol (20 ml) then D(−)tartaric acid (0.9 g; 0.006 mole) is added. The mixture is heated to complete dissolution, cooled to 15° C., stirred at 15° C. for 1 hour, filtered. The solid is recrystallized from 95% ethanol (20 ml) to obtain 1.00 g of salt having m.p. 176°–7° C.; $\alpha^{20}_D$ −113.3° C. in water (lit m.p 173°–4° C.; $\alpha^{20}_D$ −115° in water). 50.5% yield.

The solid (600 mg, 0.0015 mole) is dissolved in water (10 ml), made alkaline with NaOH and extracted with ether (2×10 ml).

The organic extract is dried over anhydrous $Na_2SO_4$, filtered and evaporated to dryness to obtain a residual oil (369 mg; 99% yield) identified as (−)-eserethole by means of I.R., $^1$H-NMR, mass spectra and by comparison with an authentic sample.

$\alpha^{20}_D$ −101.2° (C=0.5% in ethanol)

It is evident that, with only one recrystallization, according to this example, 25 g of (−)-eserethole can be obtained from 100 g of racemate.

EXAMPLE 2

Use of N-benzoyl-L-glutamic acid (±)-Eserethole (2.46 g; 0.01 mole) is dissolved in acetone (15 ml) then N-benzoyl-L-glutamic acid (1.43 g; 0.006 mole) is added. The solution is added to ethyl ether until turbid and the mixture is stirred at room temperature overnight. The solid is filtered, suspended again in acetone, stirred 1 hour, filtered, dried under vacuum. 1.83 g of a salt are obtained, having m.p. 128°–9° C.; $\alpha^{20}_D$ −75,0° (C=0.5% in $H_2O$). 73,6% yield.

1 g of salt (0.002 mole) is treated as described in Example 1, to obtain (−)-eserethole (490 mg; 98% yield) having $\alpha^{20}_D$ −100.8° (C=0.5% in ethanol)

Following the above procedure, therefore—with a single washing of the first precipitation salt—36 g of (−)-eserethole are obtained from 100 g of racemate.

EXAMPLE 3

Use of D(+)malic acid (±)-Eserethole (2.46 g; 0.01 mole) is dissolved in 95% ethanol (20 ml) then D(+)malic acid (0.81 g; 0.006 mole) is added. The mixture is heated to complete dissolution, cooled to 15 ° C., filtered.

The solid is recrystallized from 95% ethanol (20 ml) to obtain 0.72 g of salt having m.p. 160°–1° C.; $\alpha^{20}_D$ −105.8°. 38% yield.

570 mg of salt (0.0015 mole) are treated as described in Example 1, to obtain (−)-eserethole (360 mg; 98% yield) having $\alpha^{20}_D$ −100.3° (C=0.5% in ethanol)

In this case, therefore, from 100 g of racemate, about 18 g of (−)-eserethole are obtained.

We claim:
1. A process for the preparation of (−)-eserethole of formula (I)

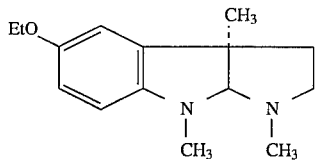

having $\alpha_D^{20}$ between −100.3 and −101.2 which comprises the steps
1) reacting a mole of a racemic mixture of (±)-eserethole, or a mixture of (+)- and (−)-eserethole in which the latter enantiomer prevails with 0.5–0.7 mole of a resolution agent, with which (−)-eserethole gives a diastereomer salt less soluble than (+)-eserethole, whereby the salt of said resolution agent and (−)-eserethole is obtained as a solid;
2) dissolving said solid in water, adding alkali, extracting with an organic solvent to obtain an extract and recovering pure (−)-eserethole from said organic extract.

2. The process according to claim 1, wherein said salt obtained in step 1) is recrystallized once from 95% ethanol.

3. The process according to claim 1, wherein said resolution agent is a member selected from the group consisting of D-(−)-tartaric, D-(+)-malic and N-benzoyl-L-glutamic acids.

4. The process according to claim 1, wherein said resolution agent is used in an amount of 0.6 mole per mole of said enantiomeric mixture or said mixture of (+) and (−)-eserethole.

5. The process according to claim 4, wherein N-benzoyl glutamic acid as the resolution agent is added to said racemic mixture dissolved in acetone to obtain a solution, ether is added to said solution to obtain a precipitate, said precipitate is purified by suspension in acetone, filtering the precipitate, said precipitate is dissolved in water, the solution made alkaline and extracted with ether and pure (−)-eserethole is recovered from the ether extract.

* * * * *